(12) United States Patent
Kopp

(10) Patent No.: US 8,123,521 B1
(45) Date of Patent: Feb. 28, 2012

(54) DEVICE FOR THE REGISTRATION OF THE POSITION OF A PROTRUDING MANDIBLE

(75) Inventor: Hans-Peter Kopp, Pfalzgrafenweiler (DE)

(73) Assignee: ERKODENT Erich Kopp GmbH, Pfalzgrafenweiler (DE)

( * ) Notice: Subject to any disclaimer, the term of this patent is extended or adjusted under 35 U.S.C. 154(b) by 0 days.

(21) Appl. No.: 13/096,120

(22) Filed: Apr. 28, 2011

(30) Foreign Application Priority Data

Feb. 24, 2011 (DE) .......................... 10 2011 000 925

(51) Int. Cl.
*A61C 19/05* (2006.01)
(52) U.S. Cl. .......................................... 433/68; 433/214
(58) Field of Classification Search .................... 433/37, 433/41, 42, 44, 68, 69, 72, 214; 33/513
See application file for complete search history.

(56) References Cited

U.S. PATENT DOCUMENTS

| | | | | |
|---|---|---|---|---|
| 3,686,759 A | * | 8/1972 | Pross geb. Hogreve | 433/37 |
| 4,602,905 A | * | 7/1986 | O'Keefe, III | 433/41 |
| 5,154,609 A | * | 10/1992 | George | 433/68 |
| 7,832,403 B2 | * | 11/2010 | Halstrom et al. | 128/848 |
| 2011/0232652 A1 | * | 9/2011 | Levendowski et al. | 128/848 |

FOREIGN PATENT DOCUMENTS

WO 93/01761 2/1993

* cited by examiner

*Primary Examiner* — Ralph Lewis
(74) *Attorney, Agent, or Firm* — Renner, Otto, Boisselle & Sklar, LLP

(57) ABSTRACT

A device for the registration of a mandibular position that is protruded relative to the normal position, with an impression plate that is flat on both sides and whose shape corresponds to the bite of the upper and the lower jaw, whose inner and outer contour is U-shaped, that comprises, in the area of the limbs of the U, finger-like registration surfaces that extend from the inner contour to the outer contour and are arranged at a distance from each other, and that is capable of limited elastic deformation in this area. Centered in relation to the limbs of the U, bite cones for accepting the upper incisors are arranged on the upper surface of the impression plate. A shaft that is of one piece with the impression plate, is centered on the impression plate, extends in an extension of the bite cones, serves for the manipulation as well as a holder of an element that can be moved in the longitudinal direction relative to the shaft, can be moved in a longitudinal slot, and has bite cones on its underside for accepting the lower incisors. Due to its thinness and deformability, the device permits the production of removable registrates with only a small increase of the occlusal height. Due to the chosen thickness of the device it is ensured that no additional bite position change will occur in appliances to be manufactured later.

13 Claims, 6 Drawing Sheets

DEVICE FOR THE REGISTRATION OF THE POSITION OF A PROTRUDING MANDIBLE

CROSS-REFERENCE TO RELATED APPLICATION

The present application claims priority under 35 USC §119 to German Patent Application No. 10 2011 000 925.6 filed Feb. 24, 2011, the entire disclosure of which is incorporated herein by reference.

TECHNICAL FIELD OF THE INVENTION

The invention concerns a device for the registration of the position of a mandible that is protruding in relation to a normal position.

DESCRIPTION OF THE RELATED ART

Such registration gauges are known as protrusion gauges. The registration serves as impression bite for several oral appliances that are manufactured in dental medicine and gnatho orthopedics. These include, for example, occlusion splints, anti-snore splints (mandibular advancement splints), gnatho-orthopedic appliances such as Herbst splints for the treatment of patients with retruded mandible, etc.

From WO 1993/001761, a device for bite registration is known where an impression plate with two opposing flat surfaces is used whose shape corresponds to the bite of the mandible and the maxilla and which represent a flattened, hollowed semicircle that is to be inserted into the mouth of the patient, with its ends close to the molars and its center part close to the upper incisors. A flat extension is provided in the form of a shaft extending in the longitudinal direction, which is of one piece with the impression plate, protrudes from the center of this impression plate, and is attached non-permanently to a measuring arm. This measuring arm is able to slide in the longitudinal direction relative to the shaft and comprises a bite notch, just like the shaft. The shaft and the measuring arm are arranged relative to each other in such a way that the bite notches are opposite from each other so that the patient is able to bite into them with the upper and lower incisors. By sliding the measuring arm that can be fixed in position relative to the shaft by means of a screw, the different positions of the maxilla and the mandible can be fixed. The device is made of metal and of rigid construction for repeated use with patients.

Movement of the patient's mandible in the longitudinal direction displaces the measuring arm. In conjunction with a calibrated scale it is possible to precisely determine the position of the teeth of the maxilla and the mandible and to measure the maximum retruded and the maximum protruded position of the mandible on a millimeter scale, thereby determining and setting an optimal value for the patient. The impression of the maxilla and the mandible is taken by means of the impression compound that can be placed on both sides of the impression plate.

It is considered to be a disadvantage of this and other known protrusion gauges that, due to their thickness and rigidity, they lead to a significant increase of the occlusal height that can only be taken into account insufficiently in the later layer thickness of the oral appliance to be manufactured. As a result, the appliance causes a change in the occlusal position. Another disadvantage is that the registrate, i.e. the impression, for the set-up of the models always remains on the gauge which makes their handling significantly more difficult.

SUMMARY OF THE INVENTION

Therefore, the invention addresses the problem of proposing a protrusion gauge where an increase of the occlusal height during the registration is avoided and where the registrate can be used without the gauge during the subsequent set-up of the models.

According to the invention, this problem is solved by a device with the characteristics of the main Claim. Additional advantageous implementations are given in the related claims.

According to the invention, the device for the registration of the protruded mandibular position comprises an impression plate that is flat on both sides, whose shape corresponds to the bite of the upper and the lower jaw, and whose inner and outer contour is U-shaped. In the area of the limbs of the U, the impression plate has finger-like registration surfaces that extend from the inner contour to the outer contour, are arranged at a distance from each other, and are formed by recesses in the impression plate that extend inward from the outer contour. In addition, the impression plate is capable of limited elastic deformation in this area so that the associated limb of the U as a whole as well as the individual lamellae are able to conform to a curved masticatory surface on the upper and/or lower jaw. In addition, centered in relation to the limbs of the U, twin bite cones for accepting the upper incisors are arranged on the upper surface of the impression plate.

In addition, the device comprises a shaft that is of one piece with the impression plate, is centered on the impression plate, and extends in an extension of the twin bite cones. This shaft serves for the manipulation of the device as a whole as well as a holder of an element that can be moved in the longitudinal direction relative to the shaft, can be moved in a longitudinal slot of the shaft, and also has twin bite cones on its underside for accepting the lower incisors.

The twin bite cones for incisors of the upper and the lower jaw consist essentially of a notch of defined configuration for the precise fixation of the teeth. The notch may also be configured differently in accordance with the prior art. In this case, cones arranged at an angle to each other were provided so that a recess with a V-shaped cross-section is formed between the cones for accepting the incisors, with the cones each advantageously protruding from the surface carrying the cones, thereby keeping the edge-to-edge occlusal height at a minimum. With the device according to the invention, the edge-to-edge occlusal height is less than twice the thickness of the impression plate in this area.

Typically, the appliances referred to above are made from an upper jaw and lower jaw splint. These splints lead to an increase of the occlusal height that is anticipated during the registration by the chosen thickness of the gauge, thereby ensuring to a high degree that no additional change of the bite position will occur with the later appliance. With a rigid registration gauge, the curvature of the masticatory plane leads to a significant increase in the occlusal height. However, the design of the device according to the invention permits a precise registration, although the impression plate easily adapts to this curvature due to the elasticity of its design. The impression plate is implemented in such a way that the registrate that is usually applied as silicone by means of an automix syringe can be pulled off the device after it has been removed. For this purpose, according to an advantageous implementation of the invention, the registration surface and the material thickness are conical, tapering towards the outer contour, in order to make the pulling off and the putting on of the registrate optimal. This means that a possible spring-back of the impression plate does not cause a permanent deformation of the registrate because it returns to its original shape due to its memory. The registrates can be used freely between the models without the protrusion gauge. This possibility of non-destructive removal from the gauge and, if necessary, a precise repositioning on the gauge permits a registration that corresponds considerably better to the later appliance.

Advantageously, the movable element is implemented as a slide with a slide plate carrying the bite cones and an actuation plate arranged on the opposite side above a rib extending in the longitudinal direction, in order to ensure, in a material-saving way, the desired function for the movement of the lower jaw and an optimal guidance of the movable element.

Also, the longitudinal slot in the shaft at the end facing away from the impression plate is advantageously equipped with a recess that corresponds to the actuation plate and through which the actuation plate can be inserted. The entire device is therefore implemented as an element made of two parts where the movable element with the actuation plate can be inserted simply through the shaft molded onto the impression plate and can then be moved in the longitudinal direction to the desired position.

Advantageously, in addition to the markings provided on the shaft, usually in the form of a millimeter scale, an additional marking is provided on the actuation plate as an indicator of the individual setting. In order to prevent the movable element from being movable in the longitudinal direction without resistance, the shaft—facing that side of the slide plate carrying the bite cones for the lower jaw incisors and in the area of the bite cones for the upper jaw incisors located on the other side—has a double set of serrations arranged transversely to the longitudinal direction that are engaged by corresponding raised elements on the slide plate that are staggered by half a division. It proved to be practical to make the serrations on the shaft correspond to the markings on the shaft, thereby ensuring simple locking in correspondence to the markings of the scale, with the staggering of the raised elements causing the division with reference to the locking to be halved.

Advantageously, for the purpose of its stability and enhanced guidance of the slide plate, the shaft comprises, at least partially, an edge following its contour on its underside, with the shaft additionally comprising in the area in which the slide is movable a longitudinal recess in order to keep the entire edge-to-edge occlusal height as low as possible.

According to a preferred implementation, the impression plate and the shaft as well as the movable element are made of a tough elastic synthetic material such as polyamide or polypropylene in order to achieve the desired thickness and elasticity. The protrusion gauge according to the invention is therefore only suitable for a one-time use with a patient. Advantageously, the material thickness at least in the area of the inner contour of the impression plate is 0.8 to 1.2 mm, preferably 1 mm, tapering in the area of the finger-like registration surfaces to 0.6 mm at the outer contour.

In the following, the invention is explained with reference to an embodiment in conjunction with the attached drawings. Individual characteristics of the invention may be realized either individually by themselves or in combination with other characteristics in embodiments of the invention.

DETAILED DESCRIPTION OF THE INVENTION

Figure 1:
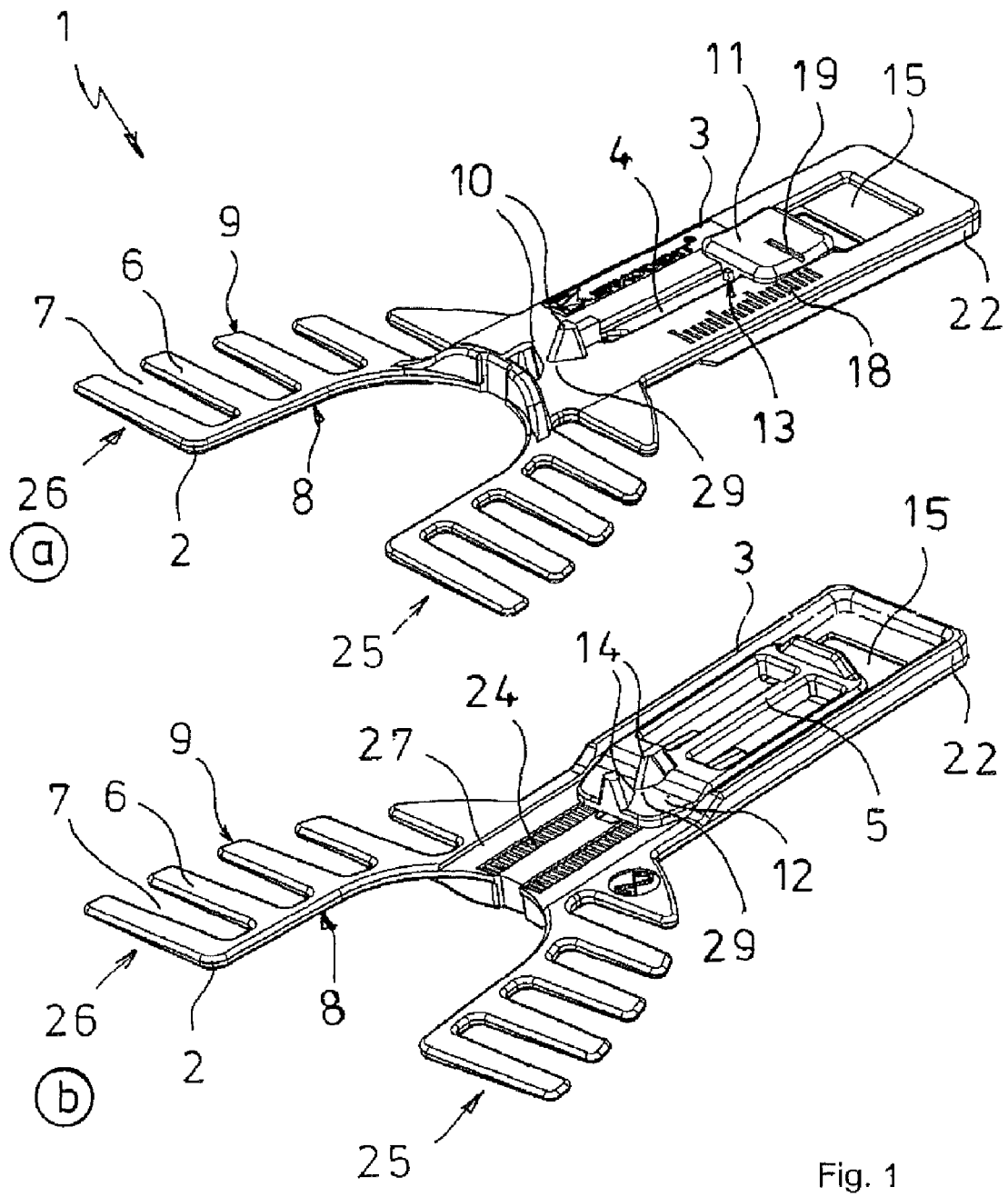
FIG. 1 shows a perspective view of a protrusion gauge according to the invention from the top (FIG. 1a) and from the bottom (FIG. 1b)
Figure 3:
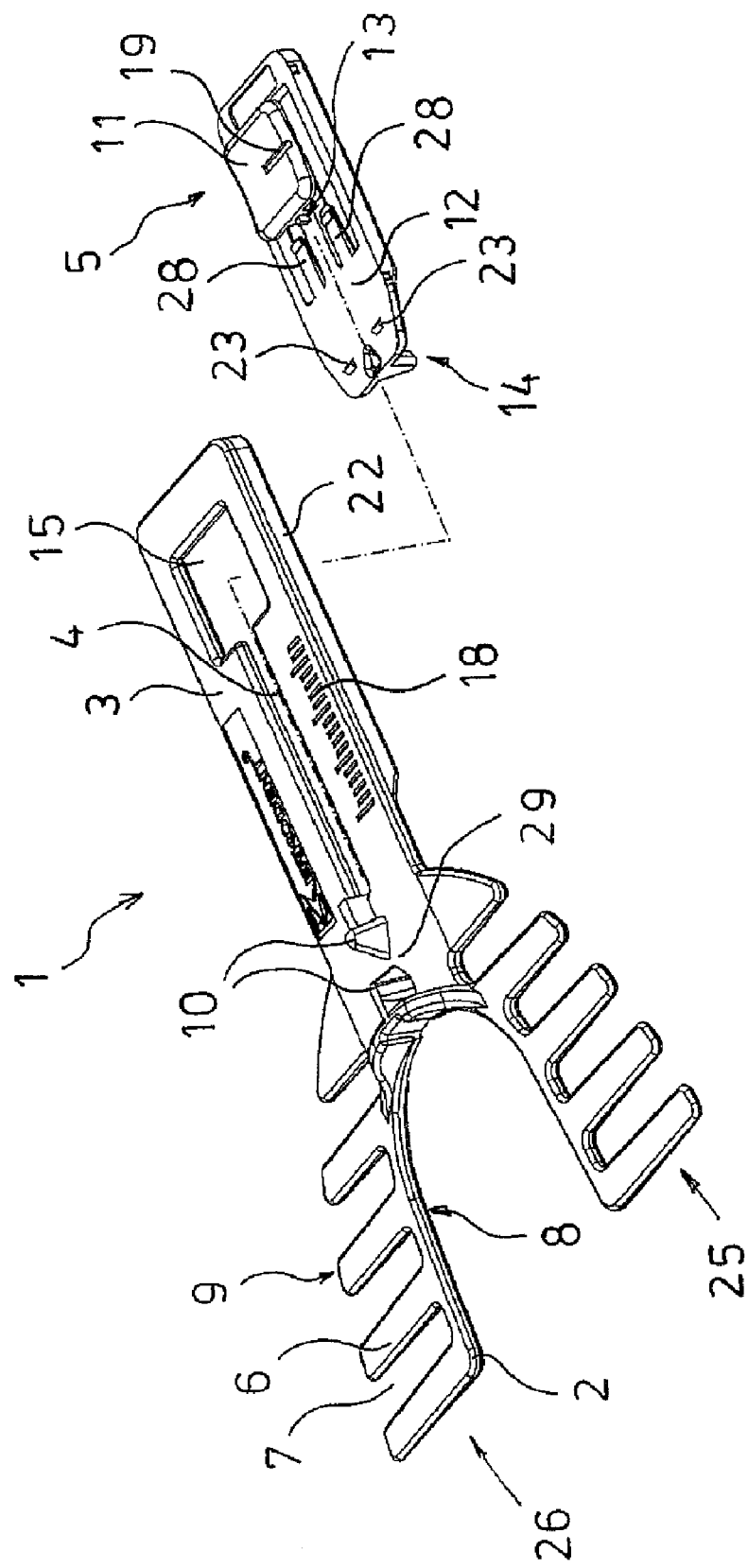
FIG. 3 shows a perspective view of the impression plate with shaft and of the movable element, as well as the method of assembly.

FIG. 1 shows the protrusion gauge 1 with an impression plate onto which a shaft 3 is molded. In the shaft 3, a longitudinal slot 4 is located in which a slide 5 can be moved by means of the actuation plate 11. The impression plate 2 is U-shaped, thereby forming two U-limbs 25 and 26 that comprise on their base centered twin bite cones 10 forming a bite notch 29 for the center of the incisors of the upper jaw. On the limbs 25 and 26, the impression plate 2 has elastic finger-like registration surfaces 6 with cone-shaped recesses 7, resulting in a comb-like outer contour 9 and a closed inner contour 8. The twin bite cones 10 for the center of the incisors of the upper jaw are located centered in the extension of the shaft 3 on the top side. Also on the top surface of the shaft 3, there is a millimeter scale 18. At the end of the shaft 3, the longitudinal slot 4 changes to a recess 15 whose dimension corresponds to the actuation plate 11 so that the slide 4 can be connected with the shaft 3 as shown in FIG. 3. At the rear section of the shaft, an edge 22 following its contour for increasing the stability and for guiding the slide 5 is molded onto the shaft.

FIG. 1b shows the protrusion gauge from below with the slide 5 that comprises twin bite cones 14 forming a bite notch 29 for the lower jaw. In this view, the serrations 24 with two parallel strips that are engaged by raised elements 23 (FIG. 2) for catching the slide 5 can be seen. In addition, a step 27 can be seen that indicates a lower material thickness in this area and also indicates a recess so that the edge-to-edge occlusal height in the area of the two bite cones 10 and 14 in the embodiment amounts to 1.8 mm. For understandable reasons, this measure should be as small as possible because it influences the occlusal height increase.

Figure 2:
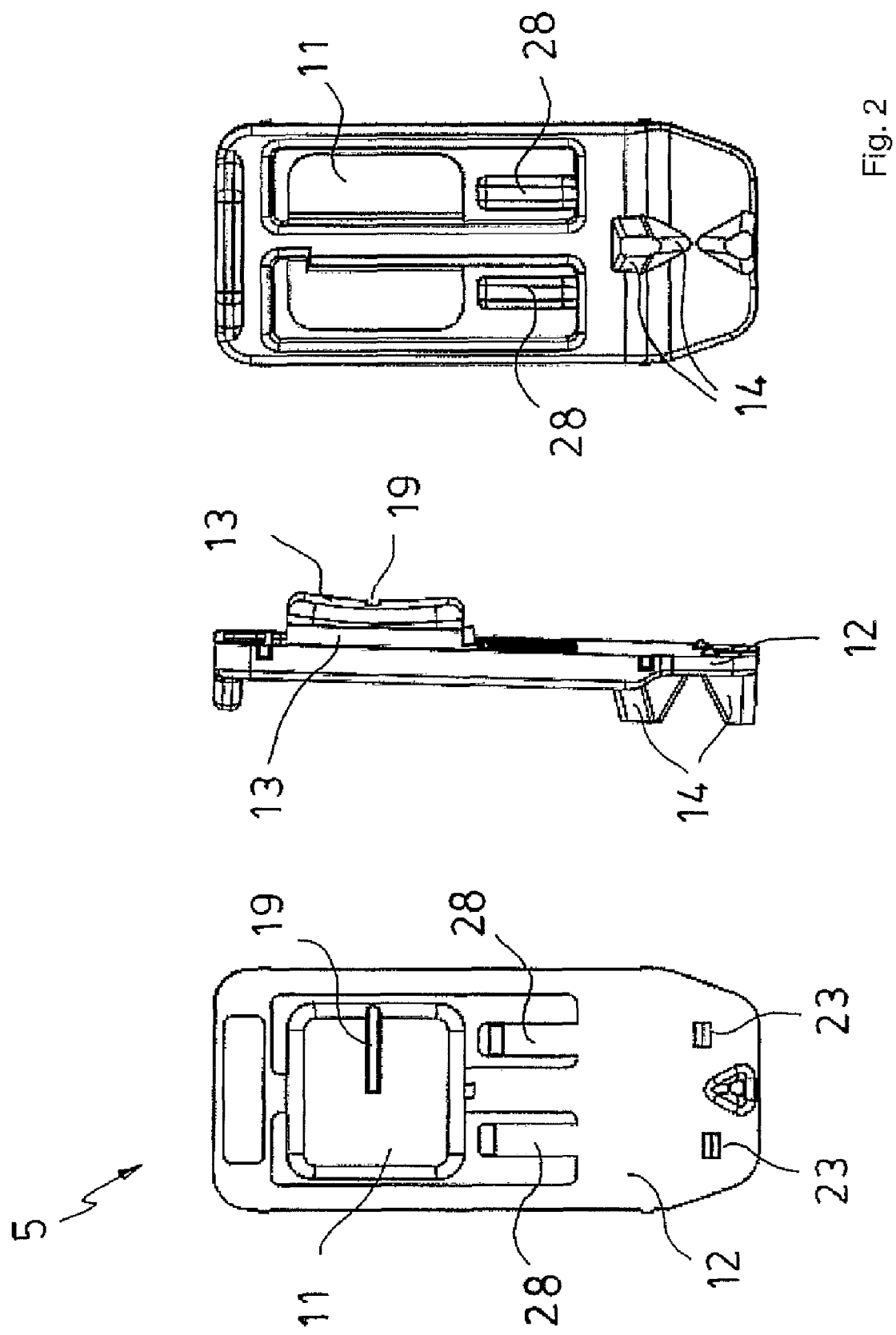
FIG. 2 shows the movable element of the protrusion gauge in both top views and one longitudinal lateral view.

The slide shown in FIG. 2 comprises a slide plate 12 on whose underside the twin bite cones 14 for the incisors of the lower jaw are arranged. The actuation plate 11 is connected with the slide plate 12 by means of a rib 13 on the top side. On the slide plate 12, spring arms 28 are arranged that generate a slight counter pressure against the shaft 3 and also compensate tolerances. On the same side of the slide plate 12, two raised elements 23 are located that engage corresponding serrations 24 on the underside of the shaft 3. The serrations correspond to the millimeter gradations of the scale 18 and provide for easy locking in the selected position. A smaller division is achieved by the staggering of the two raised elements 23 by half of the serration 24.

FIG. 3 shows the impression plate with the shaft 3, as well as the slide 5 in a position separated from it. As indicated by the dotted line, the slide 5 is guided with the actuation plate 11 through the recess 15 in the shaft 3 so that afterwards the slide 5 is movable with the rib 13 in the longitudinal slot 4 of the shaft 3.

Figure 4:
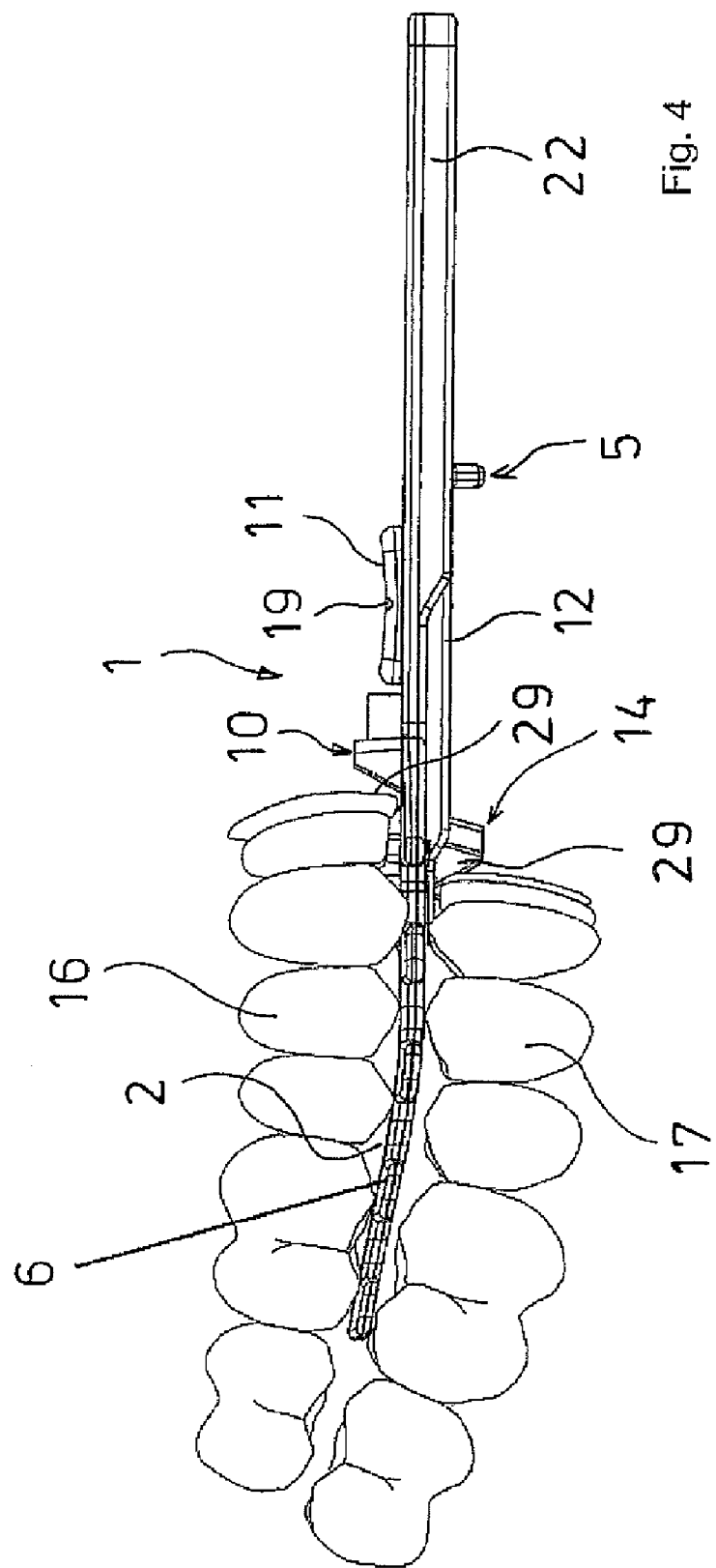
FIG. 4 shows, by way of example, the upper and lower jaw with the protrusion gauge with deformed impression plate.

FIG. 4 shows the elastic deformability of the impression plate 2 that in this Figure is adapted to the masticatory surface of an upper jaw 16 and a lower jaw 17. The upper jaw 16 is positioned with the incisors in the bite notch 29 between the twin bite cones 10, and the lower jaw 17 is positioned with the incisors in the bite notch 29 between the twin bite cones 14 on the slide 5 of the protrusion gauge 1.

Figure 5:
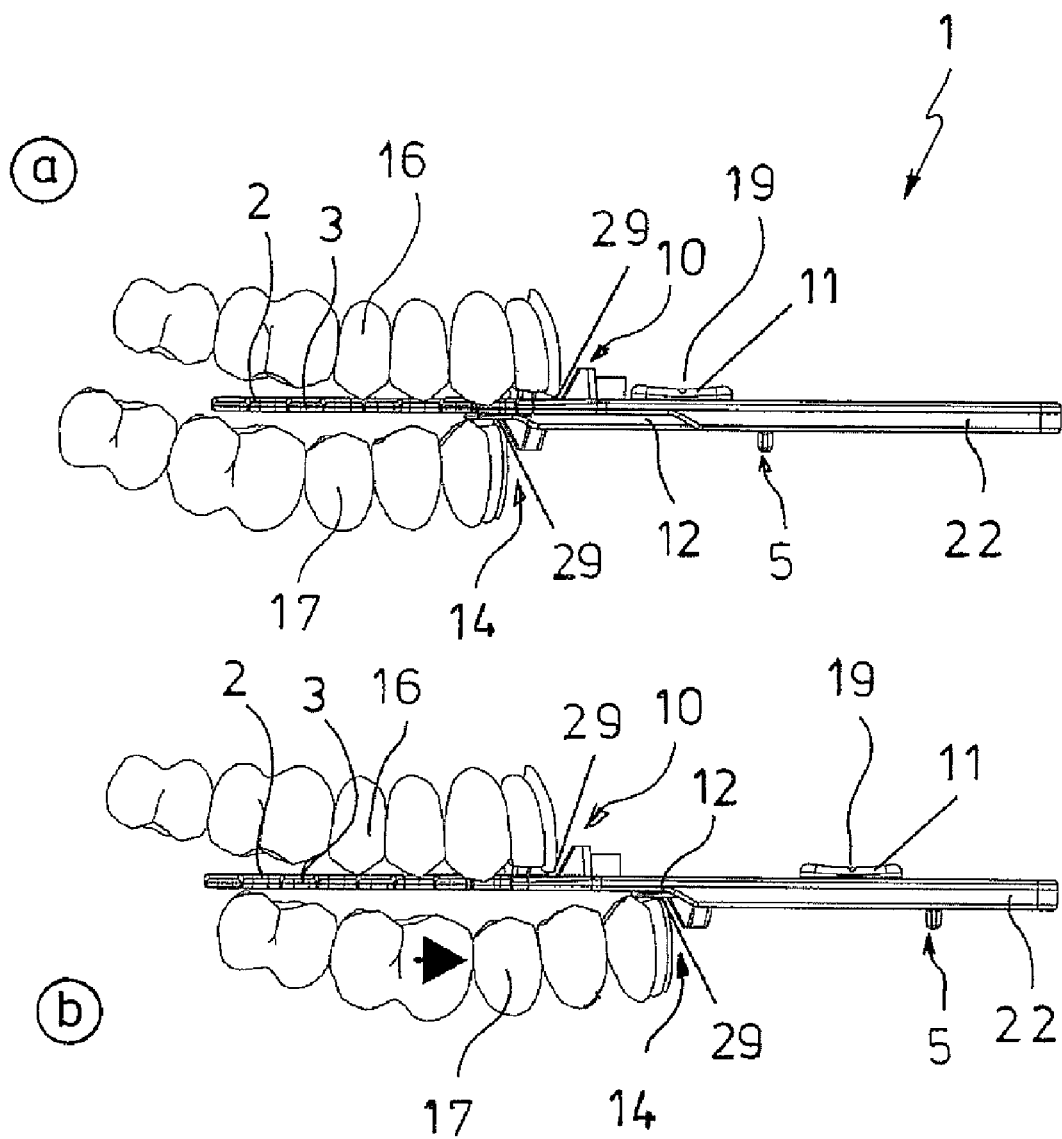
FIG. 5 shows the upper and lower jaw with the protrusion gauge located in between in the starting position (FIG. 5a) and in a position with protruded lower jaw (FIG. 5b)

FIG. 5 shows two different positions of a lower jaw 17 relative to the upper jaw 18 with the protrusion gauge 1 positioned in between. The incisors of the upper and the lower jaw are positioned in the associated bite notches between the twin bite cones 10 and 14, respectively. FIG. 4a shows the normal condition of the lower jaw 17 with a corresponding position of the slide 5, and FIG. 4b shows the condition of the lower jaw 17 protruded in the direction of the arrow, with an appropriately shifted slide 5. The Figures also show that the edge-to-edge occlusal height, i.e. the gap between the teeth caused unavoidably by the protrusion gauge, does not represent the sum of the material thicknesses of the shaft 3 and the slide plate 12 but, due to the fact that the recess for the slide plate 12 formed in the shaft by the step 27, is smaller. In this embodiment the edge-to-edge occlusal height is 1.8 mm, as stated above, with a shaft thickness and a slide plate thickness of 1 mm each.

Figure 6:
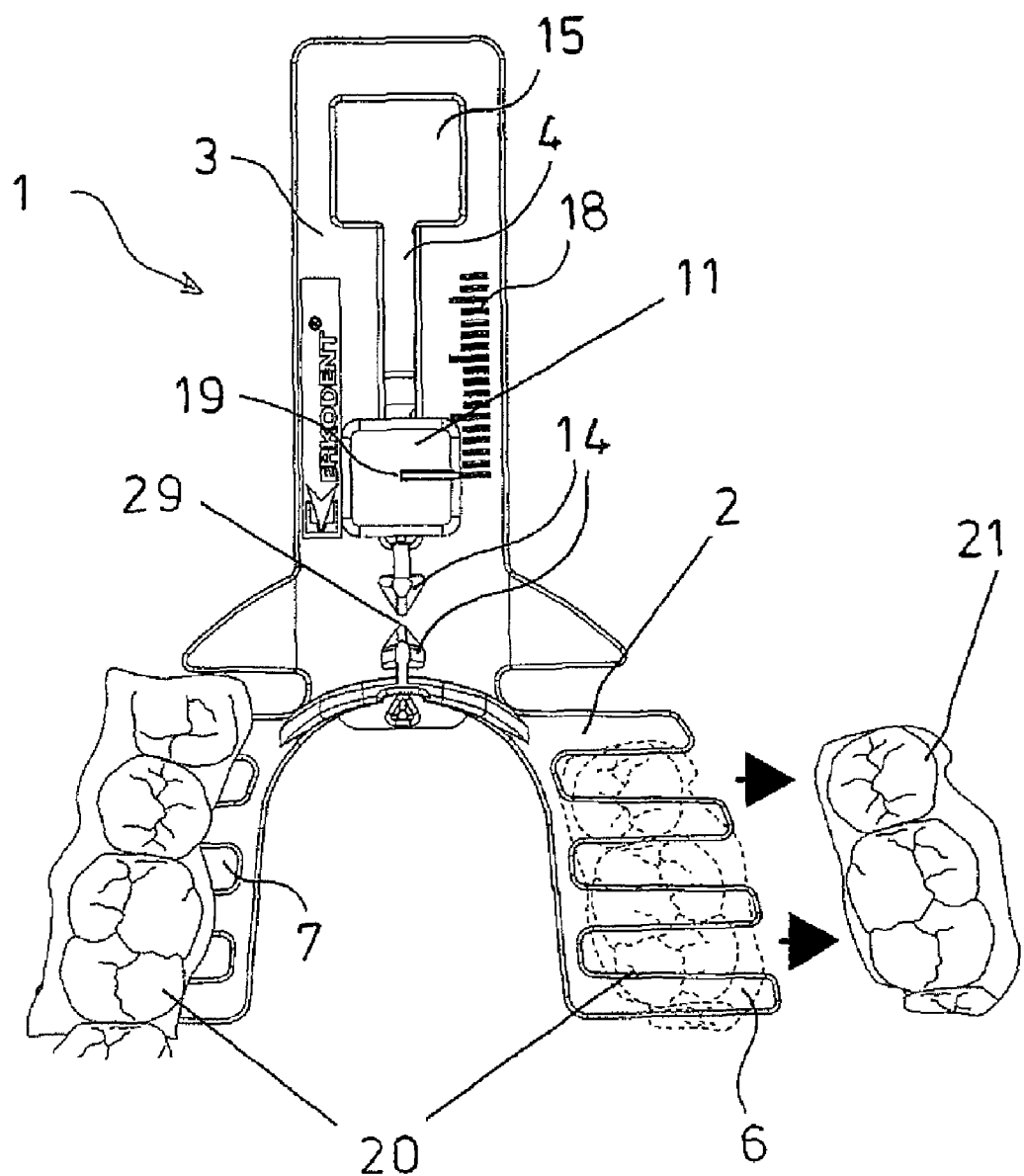
FIG. 6 shows the protrusion gauge with registrates in still fixed condition and in the condition as removed from the protrusion gauge.

FIG. 6 shows a top view of the protrusion gauge 1 with a registrate 20 on the impression plate 2, and a registrate 21 that has been pulled off the impression plate 2. As described above, the registrate can be pushed back onto the impression plate 2 at any time. However, during the manufacture of appliances, the registrate is used without the protrusion gauge. Due to the memory of the silicone material used for this, with a curved impression plate 2, the registrate also returns to its starting position after its removal.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. A device for the registration of the position of a mandible that is protruding in relation to a normal position, with
   an impression plate that is flat on both sides and whose shape corresponds to the bite of upper and lower jaw and that comprises an inner and outer contour that is U-shaped, and that, in the area of the limbs of the U, has finger-like registration surfaces that extend from the inner contour to the outer contour and are arranged at a distance from each other, said impression plate being capable of limited elastic deformation in this area and carrying on its top side, centered in relation to the limbs of the U, bite cones for accepting upper jaw incisors, and
   a shaft that is of one piece with and centered on the impression plate, extending in an extension of the bite cones, said shaft serving for the manipulation and holding of an element that can be moved in the longitudinal direction relative to the shaft, is movable in a longitudinal slot, and also has bite cones on its underside for accepting the lower incisors.

2. The device according to claim 1, wherein the registration surfaces are conical, tapering towards the outer contour.

3. The device according to of claim 1, wherein the material thickness of the impression plate tapers towards the outer contour.

4. The device according to claim 1, wherein the movable element is implemented as a slide with a slide plate carrying the bite cones and an actuation plate arranged on the opposite above a rib extending in the longitudinal direction.

5. The device according to claim 4, wherein, at the end facing away from the impression plate, the longitudinal slot in the shaft has a recess that corresponds to the actuation plate and through which the actuation plate can be inserted.

6. The device according to claim 5, wherein markings are applied to the shaft (3) and the actuation plate.

7. The device according to claim 6, wherein the serrations on the shaft correspond to the marking on the shaft.

8. The device according to claim 6, wherein the shaft has on its underside, at least partially, an edge following its contour.

9. The device according to claim 5, wherein the shaft, on the side facing the slide plate carrying the bite cones for the lower jaw incisors and in the area of the bite cones for the upper jaw incisors located on the other side, has serrations arranged transversely to the longitudinal direction that consist of two parallel rows and that are engaged by corresponding raised elements on the slide plate that are staggered by half a serration distance.

10. The device e according to claim 1, wherein the impression plate and the shaft as well as the movable element are made of synthetic material.

11. The device according to claim 1, wherein, in the area of the finger-like registration surfaces, the impression plate has a thickness of 0.8 to 1.2 mm, tapering towards the outer contour to a thickness of 0.6 mm in the area of the finger-like registration surfaces.

12. The device according to claim 11, wherein, in the area of the finger-like registration surfaces, the impression plate has a thickness of 1 mm.

13. The device according to claim 1, wherein the height of the device in the area between the bite cones amounts to 1.8 mm.

* * * * *